United States Patent [19]

Kurtz et al.

[11] Patent Number: 4,501,581

[45] Date of Patent: Feb. 26, 1985

[54] METHOD FOR AUTOTRANSFUSION OF BLOOD

[75] Inventors: Leonard D. Kurtz, Woodmere; Joseph LiCausi, Port Jefferson Station, both of N.Y.

[73] Assignee: BioResearch Inc., Farmingdale, N.Y.

[21] Appl. No.: 535,033

[22] Filed: Sep. 23, 1983

Related U.S. Application Data

[62] Division of Ser. No. 290,666, Aug. 5, 1981, Pat. No. 4,424,053.

[51] Int. Cl.³ .......................................... A61M 31/00
[52] U.S. Cl. .................................................... 604/52
[58] Field of Search ............ 168/214 B, 214 E, 214 F, 168/276–278, 297; 417/328; 222/207, 385; 141/67, 258; 137/205; 604/4–7, 30, 31, 35, 37, 38, 49, 51, 52, 53, 122–125, 134, 135, 140, 141, 149, 151, 152, 367–322, 412; 210/927, 188; 55/57, 55

[56] References Cited

U.S. PATENT DOCUMENTS 4,006,745  2/1977  Sorenson et al. .................... 604/4

Primary Examiner—C. Fred Rosenbaum
Assistant Examiner—J. L. Kruter
Attorney, Agent, or Firm—Larson and Taylor

[57] ABSTRACT

A method for the autotransfusion of blood comprising, collecting the blood from a pool in a patient and subsequently returning the collected blood to the circulatory system of the patient. The method includes applying suction to a collection chamber to remove air from the chamber and aspirate blood into the chamber. After the collection chamber is filled to the desired capacity, pressure is applied to a movable wall of the collection chamber to force the collected blood out of the chamber and back into the circulatory system of the patient.

3 Claims, 2 Drawing Figures

METHOD FOR AUTOTRANSFUSION OF BLOOD

This is a division of application Ser. No. 290,666 filed Aug. 5, 1981, now U.S. Pat. No. 4,424,053.

FIELD OF THE INVENTION

This invention relates generally to an autotransfusion device and more particularly to a disposable autotransfusion device having a collection chamber and a member for forcing blood from the collection chamber.

BACKGROUND OF THE INVENTION

During certain types of surgery, especially during chest cavity surgery, the patient frequently loses large amounts of blood. Ordinarily, the lost blood is aspirated away and the patient is given a transfusion of donated blood to make up for the blood which is lost. While this system has proven to be satisfactory, there are a number of problems associated with donated blood.

In order to reduce the problems associated with donated blood, it has been proposed in the prior art to collect the blood lost from the patient and return this blood to the circulatory system of the patient. For example, in U.S. Pat. No. 3,191,600 (Everett), an autotransfusion apparatus is disclosed which includes a vacuum source and a plurality of suction tips for immersion in pools of blood. The blood is collected in a collection chamber and is returned to the patient through a one-way valve. Another autotransfusion device is disclosed in U.S. Pat. No. 3,492,991 (Dyer, Jr.) and includes a container equipped with a filter through which the blood is gravity fed back to the patient. In U.S. Pat. No. 3,993,067 (Schachet et al), an autotransfusion device is disclosed in which the blood is forced back to the patient by pressure in the collection chamber. Still another autotransfusion device is disclosed in U.S. Pat. No. 4,047,526 (Reynolds et al). This patent discloses a collection chamber in which blood is continuously aspirated. A blood bag with an outwardly urged spring is connected to the collection chamber to withdraw some of the blood therefrom. The blood collected in the blood bag is then later reintroduced into the patient.

There has also been disclosed in the prior art a spring operated device which forces blood from a blood bag into the patient. Such a device is disclosed in U.S. Pat. No. 3,565,292 (Jinotti).

While autotransfusion has been disclosed in the prior art, these devices have tended to be complicated and unwieldy. In addition, the devices have been relatively expensive and required careful upkeep.

SUMMARY OF THE INVENTION

In accordance with the present invention, a disposable autotransfusion device is provided with a collection chamber having a stationary wall and a movable wall. The collection chamber is connected to a suitable source of vacuum by a suction hose and to the pool of blood through the apsirator hose and into the collection chamber. The collection chamber or blood bag is formed of flexible material so that the side walls move inwardly when suction is applied. However, the length to cross section ratio of the blood bag is such that the side walls cannot seal together to form an hour glass configuration with upper and lower chambers sealed off from each other. Thus, with the present invention, blood entering the bag will pass to the bottom of the bag. After the collection chamber is filled to the extent desired, the hoses to the source of vacuum and pool of blood are closed off and a spring is released from its locked position to urge the movable wall toward the stationary wall. Initially, all of the air which remains in the collection chamber is allowed to bleed from the collection chamber as the movable wall moves. After this air is removed, the collection chamber is connected to the circulatory system of the patient and the spring forces the blood in the collection chamber back into the patient.

According to a preferred embodiment, the collection chamber is formed by a blood bag which is located between the stationary wall and the movable wall. In addition, the suction source is connected to the movable wall which is at the top of the collection chamber. The outlet of the suction source in the collection chamber has an inverted cone-shaped portion to facilitate air removal and to help prevent liquids from being drawn to the suction source. Located above the inverted cone-shaped portion is a float valve to prevent liquids from entering the suction source and to assist in the removal of air from the collection chamber to eliminate the air-liquid interface. A locking device is also provided to hold the movable wall against the force of the spring until the collection chamber is filled to the extent desired.

With the present invention, a relatively simple, inexpensive, and reliable autotransfusion device is provided. The autotransfusion device is provided in a sterile package so that it can be quickly and easily connected to a source of vacuum and to the patient. When the collection chamber is filled, a new sterile autotransfusion device is similarly, quickly, and easily substituted for the filled device. The self-contained spring in the filled device is then released causing the collected blood to be forced back into the patient efficiently and effortlessly. An adjustable clamp on the return hose controls the flow of blood back to the patient. After the collected blood has been returned to the patient, the inexpensive device is thrown away.

Other features and advantages of the present invention are stated in or apparent from the detailed description of a presently preferred embodiment of the invention found hereinbelow.

DETAILED DESCRIPTION OF THE PREFERRED EMBODIMENT

Figure 2:
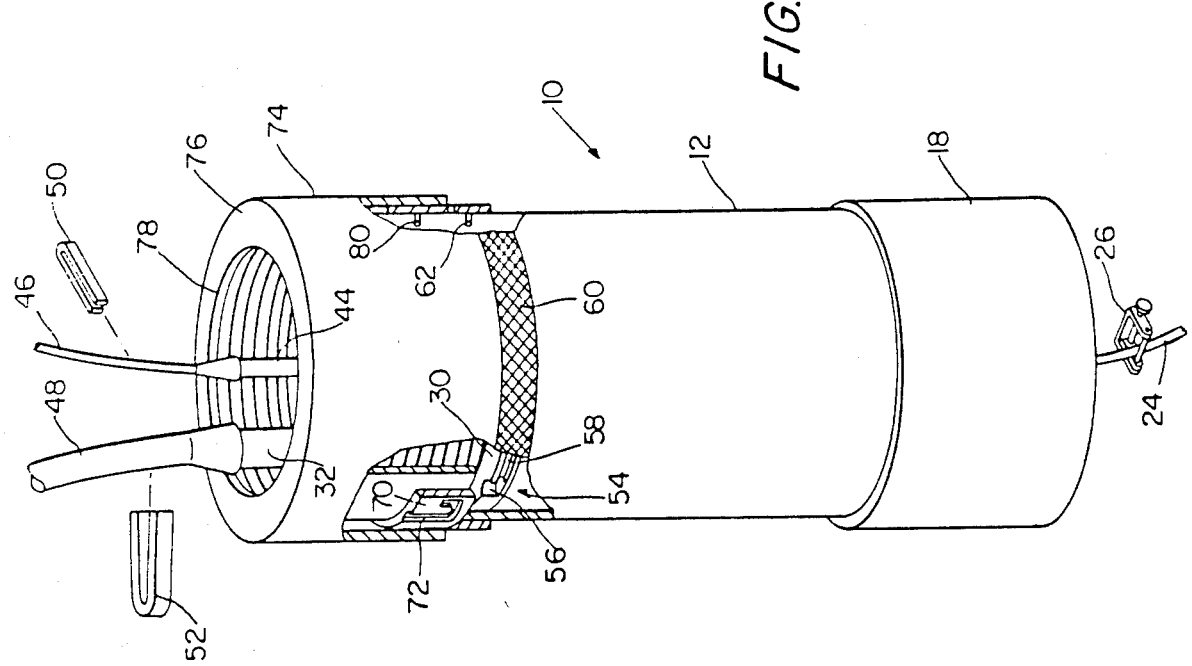
FIG. 2 is a perspective view of the autotransfusion device depicted in FIG. 1.
Figure 1:
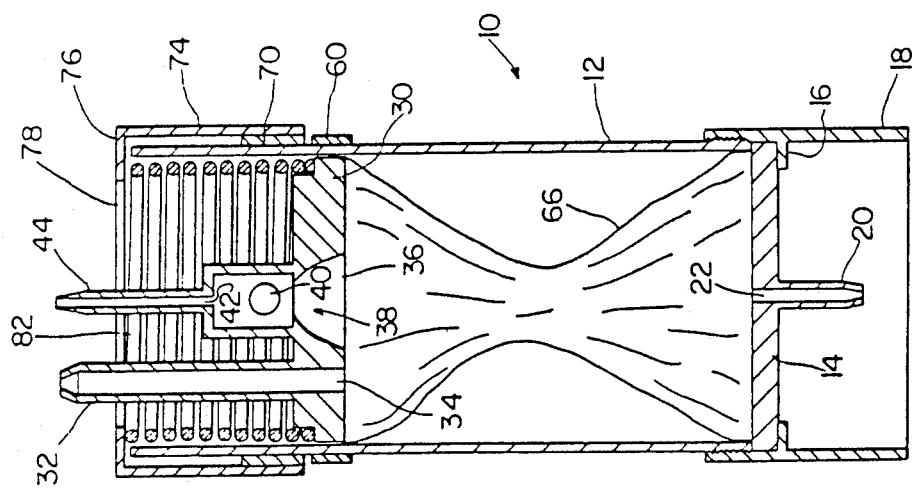
FIG. 1 is a cross-sectional elevation view of a disposable autotransfusion device according to the present.

With reference now to the drawings in which like numerals represent like elements throughout the several views, a presently preferred embodiment of the present invention is depicted in FIGS. 1 and 2 and comprises a disposable autotransfusion device 10 having a rigid cylindrical housing 12 which is preferably made of clear plastic. Located at the lower end of cylindrical housing 12 is a stationary wall 14. Stationary wall 14 is held against the bottom of cylindrical housing 12 by a flange 16 extending inwardly from a collar 18. As shown in FIG. 1, the top of collar 18 is threadably received on the bottom end of cylindrical housing 12 so that stationary wall 14 is positively held between the bottom end of cylindrical housing 12 and flange 16. A hose connection 20 containing an outlet 22 is integrally formed with stationary wall 14. As shown in FIG. 2, a return hose 24 is attached to hose connector 20. Return hose 24 has an adjustable clamp 26 attached thereto to prevent fluid flow through return hose 24 until desired.

Spaced above stationary wall 14 in cylindrical housing 12 is a movable wall 30. Integrally formed in movable wall 30 is a hose connector 32 having an inlet 34. Movable wall 30 is also provided with an outlet 36 which has the shape of an inverted cone portion. Located above outlet 36 is a float valve 38 having a float ball 40 and an outlet 42 which serves as a ball seat. Outlet 42 leads to a hose connector 44 as shown in FIG. 2. A suction hose 46 is attached to hose connector 44 and an aspirator hose 48 is connected to hose connecter 32. Both suction hose 46 and aspirator hose 48 can be clamped by clamps 50 and 52, respectively.

As shown in FIG. 2, two lock portions 54 (only one of which is shown) are located on opposite sides on the periphery of movable wall 30. Lock portion 54 includes a vertical clearing channel 56 and a horizontal locking channel 58 in the peripheral side of movable wall 30. Surrounding movable wall 30 on the outside of cylindrical housing 12 is a locking sleeve 60. Locking sleeve 60 includes two lock pegs 62 (only one of which is shown) on opposite sides of the inner periphery of locking sleeve 60. Lock pegs 62 extend through cylindrical slots (not shown) in cylindrical hosuing 12 and into respective lock portions 54. When respective lock pegs 62 extend in respective locking channels 58, movable wall 30 is held stationary. However, when locking sleeve 60 is rotate to locate respective lock pegs 62 in respective lcearing channels 56, movable wall 30 is free to move downwardly.

Disposed between movable wall 30 and stationary wall 14 is a blood bag 66. The side walls of blood bag 66 are shown in a collapsed position in FIG. 1, but it should be appreciated that blood bag 66 can extend to fill the entire space between the movable wall 30 and stationary wall 14. The upper end of blood bag 66 is attached around the periphery of movable wall 30 while the lower end of blood bag 66 is attached around the periphery of station wall 14. The blood bag 66 is so designed that when suction is applied to the bag so that the side walls tend to collapse the ratios of the cross section to length is such that the side walls cannot seal together as in an hour glass configuration.

Attached to the periphery of cylindrical housing 12 above locking sleeve 60 is a mounting sleeve 70. As shown in FIG. 2, mounting sleeve 70 has two J-channels 72 (only one of which is shown) on opposite sides thereof. A cylindrical cap 74 having a top flange 76 and a central aperture 78 extends about mounting sleeve 70 and the top of cylindrical housing 12. Cylindrical cap 74 also includes two mounting pegs 80 (only one of which is shown) which extend into respective ones of J-channels 72. Located between the top flange 76 of cylindrical cap 74 and the top of movable wall 30 is a compressed helical spring 82. In order to place helical spring 82 in cylindrical housing 12 under compression, cylindrical cap 74 is removed and helical spring 82 is located in cylindrical housing 12 on movable wall 30. Next, cylindrical cap 74 is placed on top of helical spring 82 and pushed downwardly so that mounting pegs 80 enter the long leg of J-channel 72 in mounting sleeve 70. Cylindrical cap 74 is then rotated and released so that mounting pegs 80 travel to the top of the small leg of J-channel 72. Because mounting pegs 80 are trapped in J-channel 72, cylindrical cap 74 is held to cylindrical housing 12 and helical spring 82 is maintained in compression.

In operation, disposable autotransfusion device 10 functions in the following manner. Initially, return hose 24 is clamped by clamp 26 and locking sleeve 60 is checked to make sure that movable wall 30 is securely locked in place with respective lock pegs 62 engaging locking channels 58. Next suction hose 46 is connected to hose connector 44 at one end and at the other end to a suitable source of negative pressure. It is specifically envisioned that a source of negative pressure suitable for these purposes is the negative pressure which is maintained in the collection chamber of an underwater drainage device such as the underwater drainage device disclosed in U.S. Pat. Nos. 3,363,626 and 3,363,627. Such an underwater drainage device will maintain a suction of approximately minus 20 centimeters of water which is a desirable level of negativity in order to prevent damage to formed elements of blood. An aspirator hose 48 is then attached to hose connector 32 at one end and to the pool of blood to be collected at the other end. Thus, due to the suction applied to the interior of blood bag 66, blood and air are drawn through aspirator hose 48 into the interior of blood bag 66. The blood drawn into blood bag 66 is deposited in blood bag 66 while the air is withdrawn through suction hose 46. It should be noted that the inverted cone-shaped of outlet 36 helps to prevent any liquid which may accumulate on the bottom of movable wall 30 from entering outlet 36 and being drawn into the suction source. The liquid which does accumulate on the bottom of movable wall 30 and which is drawn towards outlet 36 is not readily drawn up the incline walls of outlet 36.

As blood accumulates in blood bag 66, the collapsed side walls of blood bag 66 expand to fill the space between movable wall 30 and stationary wall 14. When blood bag 66 is filled to the desired level, aspirator hose 48 is removed from the suction source and clamped with clamp 50. At this time, another disposable autotransfusion device can be connected to the source of suction and to the patient to collect additional blood.

Before reintroducing the collected blood into the patient, it is essential to remove any air which may be contained in blood bag 66. In order to do this, locking sleeve 60 is rotated to move lock pegs 62 from respective locking channels 58 to respective clearing channels 56. This causes movable wall 30 to be pressed downward against the filled blood bag 66 by compressed spring 82. Compressed spring 82 exerts a pressure of approximately 100 to 300 mmHg. Next, clamp 50 is removed from suction hose 46 allowing air at the top of blood bag 66 to pass up outlet 36 and out of suction hose 46. However, when all of the air is gone from blood bag 66, the blood enters float valve 38 and raises float ball 40 into engagement with outlet 42. This prevents the blood in blood bag 66 from passing through suction hose 46. At this time, suction hose 46 is then clamped off with clamp 50 again.

In order to reintroduce the blood contained in blood bag 66 into the patient, return hose 24 is suitably connected to an appropriate filter and an I.V. tubing. With locking sleeve 60 already rotated so that movable wall 30 is released and being urged towards stationary wall 14 by compressed spring 82, adjustable clamp 26 is opened and used to regulate the blood flow from blood bag 66 through return hose 24 and back to the circulatory system of the patient. When all of the blood has been expelled from blood bag 66, return hose 24 is disconnected from the I.V. tubing and autotransfusion device 10 is discarded.

It should be appreciated that both the initial filling of blood bag 66 and the emptying of blood bag 66 is easily determined where cylindrical housing 12 is made of clear plastics. In addition, for convenience, disposable autotransfusion device 10 can be provided with hoses 24, 46 and 48 already attached to the respective hose connectors and with clamps 26, 50 and 52. In this manner, the entire device can be prepackaged in a sterilized container so as to be immediately ready for use when needed. The use of an underwater drainage device to provide the suction source for the present invention is also merely one example of a suitable suction source. However, it should be appreciated that the use of an underwater drainage device, such as that disclosed, provides the advantages associated with the use of the underwater drainage device with the additional advantage that a separate collection chamber is provided in which the blood can be collected and subsequently returned to the patient. The patient may be connected to the underwater drainage device in the conventional manner after the collection of blood for autotransfusion purposes.

Thus, while the invention has been described in detail with respect to an exemplary embodiment thereof, it will be understood by those of ordinary skill in the art that these and other variations and modifications may be effected in the exemplary embodiment within the scope and spirit of the invention.

What is claimed is:

1. A method of autotransfusing a patient comprising the steps of connecting a single collection chamber with a source of suction, aspirating blood from a pool of blood within the patient by an aspirating tube connected to the collection chamber, depositing the aspirated blood in said collection chamber while applying suction to the chamber to withdraw air therefrom, discontinuing the suction applied to said chamber and discontinuing the aspiration step when the collection chamber is filled with blood to the desired extent, applying a squeezing external pressure to said collection chamber, forcing the remaining air out of an outlet in the collection chamber and subsequently forcing the blood within the collection chamber into the patient's circulatory system.

2. A method of autotransfusing a patient according to claim 1 wherein the external pressure is applied to the collection chamber by forcing a movable wall of the collection chamber towards a fixed wall.

3. A method of autotransfusing a patient according to claim 2 wherein the aspirated blood is deposited within a collection chamber having collapsible walls between a stationary wall and a movable wall.

* * * * *